United States Patent [19]

Rutner et al.

[11] Patent Number: 5,164,320

[45] Date of Patent: Nov. 17, 1992

[54] METHOD FOR LYSING HARD LIPOSOMES USING POLYETHYLENEGLYCOL MONO-N-ALKYL ETHERS

[75] Inventors: Herman Rutner, Hackensack, N.J.; Abdul M. Butt, New City; Marie M. Sylvestre, Spring Valley, both of N.Y.; Josephine D. Readio, Sparta, N.J.; Lewis Pollack, Riverdale, N.Y.

[73] Assignee: Becton, Dickinson and Company, Franklin Lakes, N.J.

[21] Appl. No.: 488,168

[22] Filed: Mar. 5, 1990

[51] Int. Cl.⁵ .............. G01N 33/543; G01N 33/546; G01N 33/92
[52] U.S. Cl. ............................ 436/518; 436/533; 436/71; 436/800; 436/829
[58] Field of Search .............. 436/518, 533, 71, 800, 436/829

[56] References Cited

U.S. PATENT DOCUMENTS 4,707,441 11/1987 Fox et al. .
4,713,324 12/1987 Fox et al. .................. 435/4

OTHER PUBLICATIONS

Radany et al. (1985) The incorporation of a Purified—biochem et biophys Acta 812:695–701.

Sita et al., (1986) Effects of Triton X100—Biochem et Biophys Acta 859:165-170.
Anholt (1988) Functional Reconstitution of the Olfactory—Biochem 27:6464–6468.
Houslag et al., (1980) Dynamics of Biological Membranes J. Wiley (NY) p.30.
M. Sila et al., "Effects of Triton X-100 Concentration and Incubation Temperature on Carboxyfluorescein Release From Multimellar Liposomes", Biochimica et Biophysica Acta 859 (1986), pp.165-170.
Ethonic TM Alcohol Ethoxylates, Technical Bulletin and Product Bulletin.
Houslay et al. (1982) Dynamics of Biological Membranes, John Wiley & Sons, NY, pp. 71–81.

*Primary Examiner*—Christine M. Nucker
*Assistant Examiner*—David R. Preston
*Attorney, Agent, or Firm*—Royal N. Ronning, Jr.

[57] ABSTRACT

A method for rapidly lysing liposomes having transition temperatures in the range of 35° C. to 65° C. is provided. Such liposomes are treated with a surfactant including polyethyleneglycol mono-n-alkyl ethers such as $C_{12}H_{25}O(CH_2CH_2O)_nH$ where n=9–10, a nine mole ethylene oxide adduct of a blend of n-dodecanol, n-tetradecanol and n-hexadecanol, or other appropriate polyethyleneglycol mono-n-alkyl ether capable of causing rapid lysis. The method is applicable to fluorescence immunoassay procedures.

23 Claims, No Drawings

METHOD FOR LYSING HARD LIPOSOMES USING POLYETHYLENEGLYCOL MONO-N-ALKYL ETHERS

BACKGROUND OF THE INVENTION

The invention relates to the use of surfactants for lysing liposomes, particularly for liposomes that have high transition temperatures between 35° C. and 65° C.

Liposomes are frequently used as drug delivery vehicles which allow entrapped molecules to escape under various conditions and after various periods of time. In an article by M. Sila et al. entitled "Effects Of Triton X-100 Concentration And Incubation Temperature On Carboxyfluorescein Release From Multilamellar Liposomes", as published in *Biochimica et Biophysica Acta* 859 (1986), pp. 165–170, the lysis of various multilamellar liposomes with Triton-X is described; Carboxyfluorescein is a fluorescent dye which is commonly used as a marker to determine the rates at which water-soluble substances leak from liposomes. The three "hard" liposomes discussed in the article contained saturated phospholipids. Specifically, distearoyl-L-α-phosphatidylcholine-/cholesterol (2:1 mole ratio), dipalmitoyl-L-α-phosphatidylcholine and L-αphosphatidylcholine were tested. The carboxyfluorescein was excited by a spectrofluorometer at 490 nm and the emitted light read at 520 nm. The experiments showed that the use of Rohm and Haas' Triton X-100 TM (polyethyleneglycol (9–10) p-t-octylphenol) as a lysing agent did not result in the instantaneous destabilization of the liposome and release of the marker. The amount and rate of release were found to be dependent on the lipid composition of the liposome, the concentration of the Triton X-100, and the temperature and duration of incubation.

In contrast, U.S. Pat. No. 4,707,441 is directed to the use of liposome-compatible surfactants in connection with "soft" liposomes, i.e. those made from egg lecithin, containing unsaturated phospholipids. A number of surfactants, including those sold under the trade names Igepal (GAF Corp.) and Triton (Rohm and Haas), were tested. Some of them were found to lyse liposomes and were therefore unsuitable for the purposes described in the patent.

U.S. Pat. No. 4,713,324 discloses the lysis of liposomes by detergents or by immunological reaction. The liposome may contain one of a variety of markers such as tempocholine, a fluor and a quencher, or potassium ions. In one test, the serum levels of theophylline, a drug used to treat bronchial asthma, was determined. The "soft" liposomes for this test were formed from egg lecithin. The marker used was a chemiluminescent compound in tris (hydroxymethyl) aminomethane buffer. Triton X-100 was used to lyse the liposomes. The luminescence of intact and lysed liposomes were measured and analyzed.

While Triton X-100 was found to be effective for lysing some liposomes, particularly those having relatively low transition temperatures, it is only marginally effective upon more difficult-to-lyse liposomes, particularly those containing phospholipids with relatively high transition temperatures (e.g. stearoyl phosphatides). Sodium deoxycholate and sodium dodecylsulfate (SDS) are two other compounds frequently employed to effect lysis.

SUMMARY OF THE INVENTION

It is an object of the invention to provide a method for rapidly lysing difficult-to-lyse liposomes.

It is another object of the invention to provide a method for treating liposomes containing a marker such that signal stability is achieved within a very short period of time after initiation of lysis.

Signal reproducibility, signal enhancement and low toxicity are three additional objects of the method according to the invention.

In accordance with these and other objects of the invention, a method for lysing liposomes is provided which comprises treating the liposomes to be lysed with a surfactant having the formula $n-C_xH_{2x+1}-O(CH_2CH_2O)_yH$ wherein x represents 10 to 16 and y represents an average of 6 to 11. The liposomes to be lysed have transition temperatures in the range of 35° C. to 65° C.

The polyethyleneglycol (PEG) mono-n-alkyl ethers used in accordance with the invention provide superior lysing of liposomes having the above-referenced transition temperatures. Markers within the liposomes are accordingly rapidly released. Detecting equipment, which is used to detect the presence of the released marker, is able to generate a stable response shortly after lysing.

DETAILED DESCRIPTION OF THE INVENTION

The present invention provides a method for lysing liposomes through the use of polyethyleneglycol mono-n-alkyl ethers. The lysing may be for the purpose of releasing markers or other substances entrapped within the liposomes.

Certain types of liposomes having transition temperatures below about 35° C. are relatively easy to lyse. Conventional lysing agents are accordingly satisfactory for treating such liposomes as lysis will occur quite rapidly. Sufficiently rapid lysing may not occur when "hard" liposomes are employed, i.e. liposomes having transition temperatures between about 35° C. to 65° C. Such liposomes are preferred for encapsulating various substances, including markers used in commercial diagnostic systems which are frequently exposed to stressful conditions such as high temperatures during storage or transport. However, if the markers, such as fluorescent dyes, are not rapidly released upon addition of the lysing agent, it not only takes an undue amount of time for a stable signal from the detecting equipment to be generated, but also impairs signal reproducibility from test to test.

It has been found that surfactants having the following formula provide rapid lysing of even difficult-to-lyse liposomes:

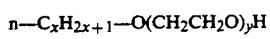

$$n-C_xH_{2x+1}-O(CH_2CH_2O)_yH$$

wherein x represents 10 to 16 and y represents an average of 6 to 11. One such compound is commercially available from ICI Americas, Inc. under the name LUBROL PX. LUBROL PX is a mixture of ethoxylated dodecyl alcohols having the following formula: $C_{12}H_{25}O(CH_2CH_2O)_nH$ where n=9–10. It has an HLB (hydrophile-lipophile balance) number of 13.8. The surfactant used in accordance with the invention should preferably have a high degree of purity, and be substantially free of contaminating peroxides, aldehydes, metals and salts.

Five criteria have been established for determining the effectiveness of lysing agents used in connection with marker-containing liposomes: (1) lysing rate; (2) signal stability; (3) signal reproducibility; (4) signal enhancement; and (5) low toxicity. The first four criteria are measured by treating a liposome containing a dye (e.g. a fluorescent dye) with the surfactant being studied and measuring the extent of lysis either by absorbance or by fluorescence. A spectrophotometer is used to detect the absorbance characteristics of the dye prior to and subsequent to lysis. The absorbance signal is quenched when the dye is in its concentrated state within the liposomes. An unquenched signal is generated when the dye is diluted in a bulk solution, where it would exist after the liposome is lysed by the surfactant. In fluorometry, the quenched signal is essentially zero and only the unquenched signal is measured.

The most important characteristic of a lysing agent as described above is the lysing rate. This rate is measured by the time it takes to lyse essentially all of the liposomes. Ideally, complete lysing occurs instantaneously.

Signal stability is measured by determining the coefficient of variation (CV) of the signal over a period of time, starting with the signal immediately after lysis. Signal reproducibility is determined by comparing the signals generated by the detecting equipment during separate tests of the same lysed solution. Signal enhancement refers to the inhibition by the surfactant of signal quenching, and is an empirical observation. Water tends to quench fluorescence. Micelles or aggregations of the lysing agent may tend to trap some of the fluorescent material, thereby shielding it from the water which would otherwise tend to quench the fluorescence.

One of the procedures in which the alkyl ethers according to the invention may be utilized is in determining theophylline (1,3-dimethylxanthine) concentration in blood serum. Theophylline, when prescribed for the treatment of asthma and other bronchial conditions, is maintained between 10–20 μg/ml. Since absorption and clearance of the drug differ from patient to patient, testing is required to monitor its concentration levels.

One test makes use of liposomes (e.g. $C_{18}:0$ distearoyl phosphatides) which contain a fluorescent dye (e.g. sulforhodamine B) and incorporate immunological properties. The dye is almost completely self-quenched within the liposomes. The immunological properties are the result of theophylline which is attached to the surfaces of the liposomes. The liposomes act as labeling agents and compete with theophylline in the patient serum for the limited numbers of binding sites on theophylline antibodies which are coated on a plastic tube. After incubation, the unbound liposomes are separated from the antibody-bound fraction by decanting and rinsing the tube. A dilute detergent is then added to the tube to lyse the liposomes and release the dye. Since the starting concentration of liposomes is constant, the resulting fluorescence is inversely proportional to the concentration of theophylline in the patient sample. This test is known as fluorescence immunoassay (FIA).

In accordance with this test, three test tubes are provided. The first tube contains theophylline liposomes within a buffer solution of deionized water, and a preservative such as 0.02% sodium azide. The liquid volume is about 1.0 ml. The second tube contains theophylline monoclonal antiserum coated upon the tube. The buffer maintains the pH at about 6.7 during subsequent mixing of the contents of the tubes. The third tube contains a dilute detergent solution in deionized water, with preservative. A liquid volume of about 2.0 ml is provided in the third tube.

A volume of about 0.05 to 0.20 ml of serum is added to the first tube which contains the liposomes. The serumliposome mixture is transferred to the second tube by coupling the first and second tubes at their open ends and inverting them several times. After incubating the coupled tubes at 25°–45° C. for about ten minutes, the tubes are uncoupled and the first tube discarded with any liquid therein. All residual incubate is also removed from the second tube by rinsing it with a saline solution and tapping the tube.

Since the test results may be affected by the length of time between washing and commencement of lysing, the detergent in the third tube should be added to the second tube as soon as possible. The second and third tubes are coupled at their open ends, inverted several times, and placed in a fluorometer for analysis.

While the above test has been conducted using a lysing agent consisting of about 1% Triton X-100, 10% tetrahydrofurfuryl alcohol, and the remainder deionized water, the toxicity and bad odor of this agent makes it undesirable.

The liposomes employed for the test procedure preferably have a relatively high transition temperature to provide superior stability under stress conditions. This characteristic also allows them to be stored without risk of damage or deterioration unless temperatures exceed at least about 55° C. The drawback, which is overcome by the present invention, is that such liposomes are more difficult to lyse. The liposome is essentially a fatty cell including a lipid bilayer which contains water and a concentrated dye. The dye is essentially self-quenched until lysis occurs. As discussed above, lysis must occur rapidly upon introduction of the lysing agent in order for the fluorometer to provide accurate and repeatable measurements.

Concentrations of $C_{12}H_{25}O(CH_2CH_2O)_nH$ (n=9–10) of 0.1 to 10%, optimally 2%, have been found to cause the rapid and complete lysis of fluor-loaded liposomes accompanied by significant fluorescense enhancement. Effective lysing of difficult-to-lyse, small digoxin liposomes, where attainment of a stable fluorescent signal has heretofore been a slow process, is very achievable using this compound. The digoxin liposomes are 50 to 350 nm in diameter.

EXAMPLE I

The data provided in Table I were obtained by following the well known procedure discussed above for fluorescent immunoassay of theophylline. In other words, the dye-containing digoxin liposomes were bound to the walls of a tube prior to introduction of the lysing agent, 2% LUBROL PX. The fluorescence signals (relative fluorescence units, RFU) generated by the fluorometer immediately after lysis, two minutes later, and two hours later are shown for three different concentrations of theophylline.

| Theoph. μg/ml | RFU Immediate | RFU 2 Min. | % Change | RFU 2 Hr. | % Change |
|---|---|---|---|---|---|
| 5 | 666 | 660 | 0.90 | 666 | 0.0 |
|   | 727 | 720 | 0.96 | 724 | 0.40 |
| 10 | 537 | 537 | 0.0 | 541 | 0.74 |

-continued

| Theoph. µg/ml | RFU Immediate | RFU 2 Min. | % Change | RFU 2 Hr. | % Change |
|---|---|---|---|---|---|
|  | 526 | 521 | 0.95 | 525 | 0.19 |
| 30 | 427 | 430 | 0.70 | 428 | 0.23 |
|  | 375 | 370 | 1.3 | 375 | 0.0 |
|  |  | x̄ = 0.80% |  |  | x̄ = 0.26% |

The above data demonstrate the stability of the signals obtained through the use of LUBROL PX, and therefore the rapid lysis of the relatively hard theophylline liposomes.

EXAMPLE II

The FIA procedure described above was again used to obtain the data shown in Table II. Digoxin liposomes bound to a test tube in accordance with standard FIA procedure were lysed with two percent concentrations of LUBROL PX. The table shows the signals generated by the fluorometer (RFU) for ten samples at ambient temperature wherein lysing was commenced at various intervals. subsequent to washing the incubated test tubes.

| Wash Interval Min. | Lysis Time RFU | | | |
|---|---|---|---|---|
|  | 0 | 1 hr. | 2 hrs. | 16 hrs. |
| 0 | 403 | 395 | 407 | 393 |
| 5 | 410 | 424 | 438 | 424 |
| 10 | 391 | 389 | 400 | 388 |
| 15 | 389 | 392 | 403 | 389 |
| 20 | 422 | 411 | 437 | 422 |
| 25 | 391 | 412 | 418 | 402 |
| 30 | 453 | 448 | 461 | 448 |
| 35 | 408 | 418 | 425 | 411 |
| 40 | 401 | 393 | 408 | 395 |
| 45 | 406 | 405 | 417 | 405 |
| x̄ | 407 | 409 | 421 | 408 |
| % C.V. | 4.7 | 4.5 | 4.6 | 4.7 |

The above data show that the addition of LUBROL PX to the bound liposomes results in an immediate, strong and stable signal. Moreover, the length of the wash interval does not have a significant effect on the test.

EXAMPLE III

Table III, shown below, demonstrates the effectiveness and signal stability achieved with compounds of the type $n-C_xH_{2x+1}$—$O(CH_2CH_2O)_yH$ (except Igepal CO-720) where x is in the range of 10–16, and y is in the range of 6–11 and optimally 9. The tests were conducted at room temperature using 2% solutions of the listed lysing agents in water. A suspension of digoxin coated liposomes averaging 113 nm in diameter and containing sulforhodamine B dye was added to the respective lysing agents. The extent of lysing was monitored photometrically by measuring absorbances at 565 nm.

TABLE III

| | LYSIS OF FREE LIPOSOMES | | |
|---|---|---|---|
| Agent | % CV[1] | % Lysis[2] | Signal[3] |
| 1. Triton X-100 | 0.47 | 98.0 | 1.03 |
| 2. Igepal CO-720 | 0.16 | 93.8 | 1.00 |

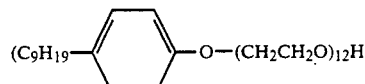

$(C_9H_{19}$—⟨phenyl⟩—$O$—$(CH_2CH_2O)_{12}H)$

| | | | |
|---|---|---|---|
| 3. Lubrol PX | 0.11 | 97.9 | 1.10 |
| 4. Polidocanol | 0.63 | 98.6 | 1.09 |
| $(C_{12}H_{25}$—$O$—$(CH_2CH_2O)_9H)$ | | | |
| 5. PO 20 Cetyl[4] | 0.38 | 54.8 | 0.56 |
| 6. PO 10 Tridecyl | 0.33 | 98.0 | 1.10 |
| 7. PO 20 Stearyl | 0.98 | 47.5 | 0.57 |
| 8. PO 10 Lauryl | 0.59 | 100.0 | 1.10 |
| 9. PO 10 Oleyl | 1.52 | 98.9 | 1.15 |
| 10. PO 20 Oleyl | 0.29 | 56.1 | 0.52 |
| 11. PO 23 Lauryl | 0.28 | 49.9 | 0.51 |
| 12. Ethonic[5] 1012-6 | 0.46 | 101.0 | 1.13 |
| 13. Ethonic 1214-9 | 0.10 | 98.6 | 1.09 |
| 14. Ethonic 1416-9 | 0.25 | 99.1 | 1.10 |
| 15. Ethonic 1416-11 | 0.58 | 91.9 | 1.03 |

[1] % CV of 20 consecutive absorbance measurements over 5 minutes starting at 0.5 minute.
[2] % lysis as expressed by the average absorbance at t = 0.5–5.5 minutes relative to the absorbance 2–5 days later. Numbers of <95% indicate incomplete or slow lysis.
[3] Absorbance ratio of 2% lysing agent relative to 2.0% Igepal CO-720.
[4] PO 20 indicates polyethyleneglycol wherein y = 20. The abbreviations used to designate agents 5–11 similarly designate polyethyleneglycol in various molar amounts.
[5] Ethonic is a trademark of Ethyl Corporation, Baton Rouge, Louisiana.

As demonstrated in Table III, the best results were obtained with LUBROL PX and with Ethonic 1214-9, a compound containing polyethyleneglycol ethers of n-dodecyl, n-tetradecyl and n-hexadecyl alcohols:

$$C_{12}H_{25}—O—(C_2H_4O)_9H$$

and $$C_{14}H_{29}—O—(C_2H_4O)_9H$$

with lesser amounts of $$C_{16}H_{33}O—(C_2H_4O)_9H.$$

Ethonic 1214-9 is the nine mole ethylene oxide adduct of an alcohol having carbon distributions of 66% C12, 27% $C_{14}$ and 7% $C_{16}$, and has an average molecular weight of 597. Its hydrophile-lipophile balance (HLB) number is 13.2.

Ethonic 1012-6 is the six mole ethylene oxide adduct of an alcohol having carbon distributions of 2% $C_8$, 75% $C_{10}$ and 23% $C_{12}$, and an average molecular weight of 428. Its HLB number is 12.4.

Ethonic 1416-9 is the nine mole alcohol ethoxylate of three alcohols having carbon distributions of 63% C14, 36% $C_{16}$ and 1% $C_{18}$, respectively. It has an average molecular weight of 623 and an HLB number of 12.8. Ethonic 1416-11 is the eleven mole ethoxylate of the same three alcohols in the same proportions as Ethonic 1416-9. It has an average molecular weight of 710 and an HLB number of 13.6.

It is apparent from Table III that compounds of the type $n—C_xH_{2x+1}—O(CH_2CH_2O)_yH$ are effective for lysing relatively small, difficult-to-lyse liposomes where x is between 10 and 16 and y is between 6 and 11. The value of y is optimally 9. If either y is greater than 20 or x equals or exceeds 18, the effectiveness of the compound as a lysing agent is clearly diminished.

Although illustrative embodiments of the present invention have been described herein, it is to be understood that the invention is not limited to those precise embodiments, and that various other changes and modifications may be effected therein by one skilled in the art without departing from the scope or spirit of the invention.

What is claimed is:

1. A method for lysing liposomes having transition temperatures in the range of 35° C. to 65° C. comprising treating the liposomes to be lysed with a surfactant having the formula $n—C_xH_{2x+1}—O(CH_2CH_2O)_yH$ wherein x represents 10 to 16 and y represents an average of 6 to 11.

2. A method according to claim 1 wherein x represents 12.

3. A method according to claim 1 wherein y represents an average of 9-10.

4. A method according to claim 1 wherein said liposomes contain fatty acid phosphatides as one of the membrane constituents of said liposomes.

5. A method according to claim 1 wherein said liposomes include $C_{18}$:0 fatty acid phosphatides as one of the membrane constituents of said liposomes.

6. A method according to claim 1 wherein said liposomes include $C_{18}$:0 distearoyl phosphatides as one of the membrane constituents of said liposomes.

7. A method according to claim 1 wherein said liposomes are digoxin coated liposomes.

8. A method according to claim 1 including the step of binding said liposomes to a surface prior to treating said liposomes with said surfactant.

9. A method according to claim 8 wherein said liposomes contain a fluorescent dye.

10. A method according to claim 1 wherein said liposomes contain a fluorescent dye.

11. A method according to claim 2 wherein said liposomes contain a fluorescent dye.

12. A method according to claim 3 wherein said liposomes contain a fluorescent dye.

13. A method according to claim 4 wherein said liposomes contain a fluorescent dye.

14. A method according to claim 7 wherein said liposomes contain a fluorescent dye.

15. A method according to claim 1 wherein said liposomes contain a fluorescent dye, including the step of measuring the fluorescence released from said liposomes subsequent to treating said liposomes with said surfactant.

16. A method according to claim 2 wherein y represents an average of 9-10.

17. A method according to claim 2 wherein said liposomes contain a fluorescent dye, including the step of measuring the fluorescense released from said liposomes subsequent to treating said liposomes with said surfactant.

18. A method according to claim 1 wherein y=9.

19. A method according to claim 1 wherein said surfactant includes a first fraction wherein x represents 12 and a second fraction wherein x represents 14.

20. A method according to claim 19 wherein y represents an average of 9 in both of said first and second fractions.

21. A method according to claim 1 wherein said surfactant includes a first fraction wherein x=12 and y=9 and a second fraction wherein x=12 and y=10.

22. A method as described in claim 1 wherein x represents 12 to 16.

23. A method as described in claim 1 including the step of treating the liposomes with an admixture of surfactants having the formula $n—C_xH_{2x+1}—O(CH_2H_2O)_yH$ wherein x represents 10 to 16 and y represents an average of 6 to 11.

* * * * *